United States Patent [19]

Norman, Jr.

[11] Patent Number: 5,723,116
[45] Date of Patent: *Mar. 3, 1998

[54] DECREASED MORTALITY OF SEVERE ACUTE PANCREATITIS FOLLOWING PROXIMAL CYTOKINE BLOCKADE

[75] Inventor: James G. Norman, Jr., Tampa, Fla.

[73] Assignee: University of South Florida, Tampa, Fla.

[*] Notice: The term of this patent shall not extend beyond the expiration date of Pat. No. 5,508,262.

[21] Appl. No.: 369,386

[22] Filed: Jan. 6, 1995

[51] Int. Cl.$^6$ .......................... A61K 45/05; A61K 38/00; C07K 1/00
[52] U.S. Cl. .......... 424/85.1; 424/85.2; 530/324; 530/351; 514/8; 514/12; 514/21
[58] Field of Search .................. 424/85.1, 85.2; 530/324.1, 351; 514/8, 12, 21

[56] References Cited

U.S. PATENT DOCUMENTS

| | | | |
|---|---|---|---|
| 4,439,196 | 3/1984 | Higuchi | 604/892.1 |
| 4,447,224 | 5/1984 | DeCant, Jr. et al. | 604/67 |
| 4,447,233 | 5/1984 | Mayfield | 604/308 |
| 4,475,196 | 10/1984 | La Zor | 371/29.1 |
| 4,486,194 | 12/1984 | Ferrara | 604/152 |
| 4,487,603 | 12/1984 | Harris | 604/152 |
| 4,522,827 | 6/1985 | Marlettini et al. | 514/671 |
| 4,902,708 | 2/1990 | Kim | 514/419 |
| 5,196,402 | 3/1993 | Braganza et al. | 514/9 |
| 5,508,262 | 4/1996 | Norman, Jr. | 514/8 |

FOREIGN PATENT DOCUMENTS

WO92/1272  8/1992  WIPO .

OTHER PUBLICATIONS

Norman et al., (1994) Interleukin—1 receptor antagonist... 95th Annual Meeting of the American Gastroenterological Assoc., New Orleans May 15–18, 1994, *Gastroenterology*, 106 (4 Suppl). A311.

Okusawa et al., *J. Clin. Invest.*, vol. 81, pp. 1162–1172, Apr. 1988.

Dinarello et al., *JAMA*, vol. 269, No. 14, pp. 1829–1834, Apr. 1993.

Michrie et al., *Arch Surg.*, vol. 125, pp. 531–536, Apr. 1990.

Aiura et al., "Interleukin–1 receptor antagoinst blocks hypotension in a rabbit model of gram–positive septic shock" *Cytokine* 4:498, (1991).

Bloedow et al., "Intravenous disposition of interleukin–1 receptor antagonist in healthy volunteers" *Amer Soc Clin Pharmacology and Therapeutics*, Mar., 1992 Orlando FL. (Abstract).

Deitch, "Multiple organ failure" *Ann Surg* 216 :117–134 (1992).

Dinarello et al., "Anticytokine strategies in treatment of the systemic inflammatory response syndrome" *JAMA* 269 :1829–1834 (1993).

Ellison et al., "Demonstration and characterization of the hemoconcentrating effect of ascitic fluid that accumulates..." *J Surg Research* 30 :241–248, (1981).

Fischer et al., "Interleukin–1 receptor blockade improves survival and hemodynamic performance.." *J Clin Invest* 89: 1551, (1992).

Granowitz et al., "Pharmacokinetics, safety and immunomodulatory effects of human recombinant interleukin–1 receptor.." *Cytokine* 4: 353–360 (1992a).

Granowitz et al., "Effect of interleukin–1 (IL–1) blockade on cytokine synthesis: I. IL–1 receptor antagonist" *Blood* 79: 2356–2363, (1992b).

Grewal et al.,"Amelioration of the physiologic and biochemical changes of acute pancreatitis using an anti–TNF–αpolyclonal antibody" *Amer J Surg* 167: 214–19, (1994a).

Grewal et al., "Induction of tumor necrosis factor in severe acute pancreatitis and its subsequent reduction after hepatic passage" *Surgery* 115(2) 213–221, (1994b).

Gross et al. "Inflammatory mediators and cytokines—new aspects of pathophysiology and assessment of severity of acute pancreatitis" *Hepato–Gastroenterol* 40: 522–529, (1993).

Guice et al., "Anti–tumor necrosis factor antibody augments edrma formation in caerulein –induced pancreatitis" *J Surg Res* 51:495–499, (1991).

Heath et al., "Role of interleukin–6 in mediating the acute phase protein response and potential as an early means . . ." *Pancreas* 66:41–45, (1993).

Hughes et al., "Induction of acute pancreatitis in germ–free . . ." *Surgery*, 117: 201–205 *Proc. 28th Annual Meeting of Pancreas Club*, (1994).

Larsen and Henson, "Mediators of inflammation" *Ann. Rev. Immunol* 1: 335–359, (1983).

Leach et al., "New perspectives on acute pancreatitis" *Scan J Gastroenteuol* 27 Suppl 192: 29–38, (1992).

Michie and Wilmore, "Sepsis, signals, and surgical sequelae (A hyypothesis)" *Arch Surg* 1225: 531–536, (1990).

Murayama et al., "Does somatostatin analogue prevent experimental acute pancreatitis" *Arch Surg* 125: 1570–1572 (1990).

Norman et al., "Rapid elevation of systemic cytokines during acute pancreatitis . . . " *Surg Forum* XLV: pp. 148–150.

(List continued on next page.)

Primary Examiner—Cecilia J. Tsang
Assistant Examiner—Abdel A. Mohamed
Attorney, Agent, or Firm—Kenneth I. Kohn

[57] ABSTRACT

A method for treating acute pancreatitis is disclosed. The method comprises administering to a patient with acute pancreatitis an effective amount of a suitable tumor necrosis factor (TNF) antagonist such as a TNF soluble receptor or a pharmaceutically acceptable salt thereof.

16 Claims, 7 Drawing Sheets

OTHER PUBLICATIONS

Norman et al., "Decreased severity of experimental acute pancreatitis by pre or post treatment . . . " *28th annual Meeting, Pancreas Club, Inc.,* (New Orleans, LA) May (1994c), p.23 (Abstract).

Noronha et al., "Alcohol and the pancreas. I. Clinical associations and histopathology of minimal pancreatic inflammation" *Am Gastroenterol.* 3: 9–18, (1988).

Kushner, in Clinical Applications of Cytokines, "Regulation of the acute phase response . . . " *Oxford University Press,* New York, NY, pp. 27–34 (1993).

Physicians'Desk Reference®: pp. 1654–1658, (1994).

Schoenberg et al., "The role of oxygen radicals in experimental acute pancreatitis" *Free Radical Biology & Medicine* 12: 515–522, (1992).

Steer, "How and where does acute pancreatitis begin?" *Arch Surg* 127: 1350–1353, (1992).

Tani et al., "Histologic and biochemical alterations in experimental acute pancreatitis induced by supramaximal . . . " *Intl J Pancreatology* 2:337–348, (1987).

Takeyama and Saitch, "Possible involvement of peritoneal macophage activation in remote . . ." *Meeting of the Society of University Surgeons,* Feb. 1994, Jackson, Miss. (Abstract #106).

Torab et al., "Clinical significance of endotoxin interleukin–6 and transferrin . . ." *Meeting of the Society of University Surgeons,* Feb. 1994, Jackson Miss. (Abstract #115).

Wakabayashi et al., "A specific receptor antagonist for interleukin–1 prevents *E. coli* induced shock in rabbits" FASEB 5: 338, (1991).

Zhu et al., "A somatostatin analogue is protective against retograde bile salt–induced pancreatitis in the rat" *Pancreas* 6: 609–613, (1991).

DECREASED MORTALITY OF SEVERE ACUTE PANCREATITIS FOLLOWING PROXIMAL CYTOKINE BLOCKADE

TECHNICAL FIELD

The present invention relates to a method for treating acute pancreatitis.

BACKGROUND OF THE INVENTION

Acute pancreatitis is a common clinical problem which remains evasive of specific therapy (Leach et al., 1992). Each year more than 210,000 admissions to U.S. hospitals are caused by acute pancreatitis. It is most often caused by alcoholism or biliary tract disease. Less commonly, it is associated with hyperlipemia, hyperparathyroidism, abdominal trauma, vasculitis or uremia. The average length of hospitalization for the disease is 12.4 days, with a significant number of patients staying much longer because of associated complications.

Chronic ethanol abuse is the most common cause of acute and chronic pancreatitis in the West, yet the pathophysiology of this disease remains poorly understood (Steinberg and Tenner, 1994). There are few medical therapies or pharmacologic agents currently available which have been shown to decrease the severity, duration, complication rate, or mortality for this common disease. Care for these patients, regardless of the etiology, remains primarily supportive, with attention directed towards maintaining an adequate circulating blood volume, supporting renal and respiratory systems, and providing adequate nutrition. This lack of specific therapy has prompted a great number of prospective trials during the past two decades in hopes of finding some way to decrease the progression and severity of this disease. To date, specific therapy remains unknown and a search for new, more effective modalities is necessary. The overall mortality for acute pancreatitis varies between 6 and 18% and can raise as high as 50% in the more fulminant form (Steinberg and Tenner, 1994; Imrie and Whyte, 1975; Jacobs et al., 1977). Interestingly, the prognosis for this disease appears more dependent upon its systemic manifestations and complications than upon the severity of the local pancreatic inflammation (Imrie and Whyte, 1975; Jacobs et al., 1977). In fact, as many as 60% of deaths from acute pancreatitis which occur within one week of onset can be attributed to adult respiratory distress syndrome (ARDS), which cannot be distinguished from sepsis-associated ARDS (Steinberg and Tenner, 1994; Jacobs et al., 1977).

It was noted in 1966 that dogs suffering from an experimental model of severe pancreatitis did not die as frequently if their abdomen was washed with Ringer's lactate to remove the pancreatic associated ascitic fluid (PAAF) (Rodgers and Carey). It was suggested that peritoneal lavage removed some toxic substance(s) within the PAAF.

During the 1970s and early 1980s, several investigators examined the toxic effect of PAAF on multiple organ systems. Fabri and colleagues conducted a number of experiments in an attempt to determine the factor or factors present in the pancreatic ascites which was responsible for the systemic effects seen during acute pancreatitis. Their studies showed that a substance was present in PAAF which was responsible for the hemoconcentrating effect, as well as hypotension seen during severe attacks (Ellison et al., 1981). They subsequently demonstrated that ARDS could be induced when the lungs of healthy animals were lavaged with small amounts of PAAF. Hepatic mitochondrial respiration and oxygen consumption was diminished in vitro when hepatic cells were exposed to PAAF (Coticchia et al., 1986; Pappas et al., 1978). This toxin, therefore, was not specific for one cell or tissue type; in fact, it has profound effects on all organ systems examined.

This "cytotoxic factor" had not been positively identified, yet several clinical studies by Ranson et al. (1978), and Stone et al. (1980) supported the presence of this group of toxin(s) in humans by showing that peritoneal lavage early in the course of acute pancreatitis could decrease the incidence and severity of systemic sequelae and decrease overall mortality. Recent studies by the applicant has documented the presence of inflammatory cytokines within pancreatic ascites (human and animal) supporting the role of these mediators in the development of systemic complications associated with acute pancreatitis.

Over the past decade, a somatostatin analog has undergone several clinical, as well as laboratory trials, in an attempt to show beneficial effects of suppressing pancreatic exocrine function pharmacologically during acute pancreatitis. The majority of investigators have shown beneficial effects only with treatment prior to the onset of pancreatitis, and disappointing results when somatostatin was given after the acute inflammatory process had started (Murayama et al., 1990; Zhu et al., 1991; Spillenaar et al., 1989).

A curious aspect of acute pancreatitis is the systemic response which is seen following inflammation initiated within the pancreas. Acute pulmonary, renal, and hepatic failure, generalized water retention, hypocalcemia, hypoxia, and acid/base disturbances are all possible complications of pancreatitis. The mechanism for the involvement of these other organ systems probably involves activation of the cytokine cascade, including interleukin-1 (IL-1), interleukin-6 (IL-6), and tumor necrosis factor (TNF) in a manner not significantly different from sepsis syndromes (Heath et al., 1993; Larson and Henson, 1983; Deitch, 1992; Michie and Wilmore, 1990; Dinarello et al., 1993). Serum levels of these peptides have been shown to correlate to a high degree with the severity of acute pancreatitis in humans, and can also be demonstrated within pancreatic ascites (Heath et al., 1993; Ellison et al., 1981). Other findings have shown that much of the intrinsic pancreatic damage seen in acute pancreatitis is due to the release of cytokines from macrophages and other white blood cells which migrate into the damaged gland (Steer, 1992; Tani et al., 1987; Van Ooijen et al., 1990; Schoenberg et al., 1992; Kelly et al., 1993; Gross et al., 1993; Guice et al., 1991; Heath et al., 1993; Norman and Franz, 1994; Norman et al., 1994a; Norman et al., 1994b; Norman et al., 1994c; Leach et al., 1992; Dinarello et al., 1993; Grewal et al., 1994a; Grewal et al., 1994b; Cioffi et al., 1993; Lowry, 1993; McKay et al., 1994; Formela et al., 1994; Dolan et al., 1994; Oppenheim et al., 1993).

Guice et al. (1989) have shown that pancreatitis-associated adult respiratory distress syndrome (ARDS) is to a large degree neutrophil mediated and is not iron-dependent or hydroxyl-radical mediated. They suggested that the process of acute pancreatitis leads to neutrophil recruitment, sequestration, and adherence to alveolar capillary endothelial cells with lung injury ultimately a result of neutrophil-generated products including cytokines. These cytokines are active in low concentrations (picomolar-femtomolar) and are not produced in the normal disease-free state. They may function as mediators in a autocrine, paracrine, and endocrine fashion, and, therefore, may induce inflammation or tissue damage locally, as well as at great distances (Dinarello et al., 1993; Cioffi et al., 1993; Lowry, 1993; Oppenheim et al., 1993).

The administration of IL-1 to rabbits (Wakabayashi et al., 1991; Okusawa et al. 1988; Ohlsson et al., 1990; Aiura et al., 1991) and primates (Fischer et al., 1991) has been shown to result in hypotension, tachycardia, lung edema, renal failure, and, eventually, death, depending on the dose. These signs and symptoms are similar to those demonstrated by patients with severe acute pancreatitis. When the serum from the IL-1 treated animals is examined, the elevation of other cytokines is evident, mimicking the levels seen in acute pancreatitis in humans (Guice et al., 1991; Heath et al., 1993).

Recent investigations have shown that serum levels of inflammatory cytokines correlate to a high degree with the clinical severity of pancreatitis. In a recent publication, Heath et al. (1993) showed significantly higher serum IL-6 levels (approximately 10-fold higher) in patients with severe acute pancreatitis than those with mild acute pancreatitis (Heath et al., 1993). These researchers demonstrated that the clinical course of those patients with higher levels of IL-6 was more complicated and protracted than those with low or undetectable IL-6. A similar study presented at the 1994 meeting of the Pancreatic Society of Great Britain and Ireland showed elevation IL-1, IL-6, and Tumor necrosis factor-$\alpha$ (TNF-$\alpha$) in all patients with severe pancreatitis which correlated very well with systemic symptoms, complications, and mortality (McKay et al., 1994).

IL-1, IL-6, and TNF-$\alpha$ can be isolated from pancreatic ascites in both humans and experimental animals (Heath, 1993; Norman and Franz, 1994; McKay et al., 1994; Dolan et al., 1994), and again, levels correlate with the severity of disease. It is interesting to note that the molecular weight of these three cytokines is between 10,000 and 25,000 daltons as suggested by Carey and associates as early as 1983.

As stated hereinabove, TNF is one of the cytokines that is elevated in pancreatitis. Takeyama and Saitch (1994) have shown that the peritoneal macrophages are activated in pancreatitis and release TNF-$\alpha$. In one study (McKay et al., 1994), increased release by activated leucocytes was associated with those patients who developed systemic complications associated with their pancreatitis. Further, in models of pancreatitis, increase in TNF was also seen mimicking the course seen in human patients. (Dolan et al., 1994; Formela et al., 1994; Norman et al., 1994a–c)

Grewal and colleagues have recently published several articles examining the role of TNF-$\alpha$ in the pathogenesis of acute pancreatitis (Grewal et al., 1994a; Grewal et al., 1994b). Their work supports previous work by Guice et al. (1991) and Dolan et al. (1994) which demonstrates that TNF-$\alpha$ is rapidly produced during acute pancreatitis and can be found in the systemic circulation. Grewal et al. have gone a step further in showing that levels of TNF-$\alpha$ are significantly higher in the portal vein than in the hepatic or femoral veins (Grewal, 1994b) and that TNF-$\alpha$ release is not dependant upon endotoxin (Kotb et al., 1994).

Applicant has also shown that TNF-$\alpha$ (as well as IL-1 and IL-6) are rapidly and predictably elevated during acute pancreatitis and that levels are highest within the pancreas itself (Norman et al., 1994a). Applicant suggest that this is evidence of cytokine production within the pancreas which may be partially cleared by the liver.

There seems little doubt now that several inflammatory cytokines are activated and detectable in pathologic concentrations in the serum and ascites of humans, as well as experimental animals, during bouts of acute pancreatitis.

This complements the large body of evidence currently available which supports the roles of IL-1 and TNF as major mediators of the systemic response to diseases such as sepsis and pancreatitis and as activators of the remaining members of the cytokine cascade (Dinarello et al., 1993). Fischer et al. 1991) demonstrated that the administration of a naturally occurring antagonist to IL-1 will significantly blunt the cytokine cascade and improve survival in baboons given a lethal dose of live bacteria. In this study, IL-1 receptor antagonist (IL-1ra) significantly attenuated the decrease in mean arterial pressure and cardiac output and improved survival over control. The systemic IL-1 and IL-6 responses observed as a result of the bacteremia were diminished significantly, correlating with a decrease in the systemic response to the sepsis.

Studies by Aiura et al. (1991) have shown that IL-1ra is protective in a rabbit model of hypotensive gram-positive septic shock. The administration of IL-1ra in this animal model has been shown to maintain mean arterial pressure compared to control, as well as decreasing lung water and maintaining urine output. This work demonstrated the role of IL-1 and the protective role of IL-1ra in gram-positive shock which was thought to be due to a separate mechanism from gram-negative shock. The common pathway for the systemic manifestations of these two different models of shock has been shown to involve IL-1 as a central mediator. Evidence is mounting for the role of IL-1 and TNF as principal mediators in a patient's clinical response to multiple different stresses regardless of the etiology (including acute pancreatitis).

Grewal et al. (1994) have shown that treatment with anti-TNF antibody therapy improves survival in an animal model of acute pancreatitis when given prophylactically. Treatment of humans with antibodies (monoclonal or polyclonal) carries significant risks. The antibodies represent a foreign protein which is itself antigenic to the recipient. This has been shown to be a problem in approximately 3–5% of all patients receiving an initial treatment with antibodies (PDR, 1994). However, the incidence of complications, including death from serum sickness, has been shown to increase to as much as 30% with repeat administration. For these reason no current manufacture of antiserum or antibodies allows the repeat administration of these proteins.

An additional theoretical problem with antibody therapy when applied to antagonism of human cytokines is that the affinity of the cytokine for its membrane bound receptor is several orders of magnitude (3 to 5) higher than is the affinity of the proposed blocking antibody for the cytokine in question. The stoichiometry dictates that the cytokine has an increased chance of binding to the receptor than to the corresponding antibody, therefore mediating its detrimental effects. Since cytokines are known to illicit their intracellular responses and subsequent detrimental effects when only a single cytokine has found its way to a membrane bound receptor, the importance of complete blockade of the circulating cytokine becomes of paramount importance. (Oppenheim, et al., 1993)

Hence, to be effective on repeated administration, an antibody should not be antigenic. In general, efforts to reduce antigenicity have included forming chimeric molecules that comprise human antibody constant domains fused with murine antibody variable domains humanizing muring antibodies so that all but the six hypervariable loops of the antibody combining site are of human sequence and, most definitively, producing human antibodies in vitro and thus bypassing the need for immunization in other species. However, these procedures are not always available, do not always provide antibody with the necessary avidity and are costly to provide. Therefore, other treatment modalities must be explored.

U.S. Pat. Nos. 4,522,827 and 4,902,708 disclose methods of treating acute pancreatitis. However, none of these patents take into effect the specific pathology of the disease, thereby proposing treatments which are not specific and are directed to the symptoms only, not the underlying mechanism.

U.S. Pat. No. 5,196,402 discloses the use of S-adenosyl methionine for the use of treatment of pancreatitis in the context of a complication in the graft rejection in pancreas transplant, a very uncommon procedure. The patent does not address acute pancreatitis as a disease in the nontransplant patient. The vast majority of cases of pancreatitis are not associated with pancreatic transplants.

From the above review, it is apparent that systemic complications associated with severe pancreatitis are mediated by pro-inflammatory cytokines. Applicant has previously shown that proximal blockade of the cytokine cascade at the level of the interleukin-1 (IL-1) receptor results in attenuated production of these inflammatory mediators and is associated with a significant decrease in the severity of pancreatitis as set forth in co-pending U.S. patent application Ser. No. 167,698 assigned to the assignees of the present invention and incorporated herein by reference. These changes are associated with a survival advantage, therefore it would be useful to increase the efficacy of proximal cytokine antagonism in order to decrease the mortality of acute pancreatitis.

Additional treatments are needed which take into account that the local, as well as systemic, effects seen during acute pancreatitis are due to activation of the cytokine cascade whereby proximal inhibition of this cascade will decrease the severity of the inflammatory process.

SUMMARY OF THE INVENTION AND ADVANTAGES

According to the present invention, a method for treating acute pancreatitis is disclosed which comprises administering to a person with acute pancreatitis an effective amount of a tumor necrosis factor antagonist such as a TNF soluble receptor (TNFsr) or a pharmaceutically acceptable salt thereof.

The invention further discloses a method for treating acute pancreatitis which comprises co-administering to a person afflicted with that condition an effective amount of a combination of TNFsr and Interleukin-1 receptor antagonist (IL-1ra) or a pharmaceutically acceptable salt thereof. In a preferred embodiment a recombinant TNF soluble receptor is used.

Both methods of the present invention have the advantage of taking into account that the local, as well as systemic, effects seen during acute pancreatitis are due to activation of the cytokine cascade and blocking that activation. Further the method of blocking, i.e., binding to soluble receptors, does not pose the problems associated with antibody treatments.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

According to the present invention, a method of treating acute pancreatitis is disclosed in which a patient with acute pancreatitis is administered an effective amount of a TNF antagonist, preferably in the form of a soluble receptor, in its monomeric or in its polymeric form such as a dimer. In a preferred embodiment recombinant tumor necrosis factor soluble receptors (rTNFsr) or a pharmaceutically acceptable salt thereof is used. In a second preferred embodiment, the method of treatment of acute pancreatitis is to co-administer rTNFsr with IL-1ra consistent with good medical practice.

Tumor necrosis factor soluble receptor (TNFsr) is a cytokine cascade blocker. In vivo, it is produced in response to the same enciting events which cause the elicitation of the agonist TNF such as trauma, sepsis and pancreatitis. It is a single molecule. The recombinant molecule (rTNFsr) can be produced as a dimer thereby increasing receptor-ligand affinity approximately 100 fold. The co-efficient of dissociation for the naturally occurring molecule is $10^{-7}$ while the coefficient of dissociation for the recombinant dimer is $10^{-11}$ (Oppenheim et al., 1993) thereby requiring a smaller dose as a therapeutic than the naturally occurring molecule. Further, the dimer structure leads to an increase of the half-life to 27 hours in vivo permitting single daily dosing (Mohler, 1994). However, any other means that decreases the coefficient of dissociation for the molecule can be used in the practice of the present invention.

There are several important aspects of the recombinant soluble TNF receptor which makes it a preferred embodiment for the antagonism of circulating TNF rather than antibodies directed against TNF. First and foremost, the protein is a recombinant form of a naturally occurring human protein and, therefore, is not generally antigenic. Phase I clinical trials conducted by Immunex Corporation utilizing healthy volunteers have shown that this protein has no antigenic effects in that the host was unable to identify it as a foreign substance. It did not cause any systemic symptoms such as fever, tachycardia or other signs associated with infusion of foreign protein.

Secondly, the soluble TNF receptor in its monomeric form has an affinity approximately equal to that of the membrane bound TNF receptor and, therefore, several orders of magnitude (3 to 5) higher affinity for the circulating TNF than does a blocking antibody directed at the same circulating TNF. Studies by both Synergen Corporation (Boulder, Colo.) and Immunex Corporation have shown that the linking of two soluble TNF receptors into a dimeric form increases the affinity for circulating TNF by approximately 100 fold, therefore circulating TNF will preferentially bind to the circulating soluble TNF receptors rather than attaching to membrane bound receptors and causing intracellular effects to be mediated.

Importantly, the second messenger system for the TNF molecule has been shown to be composed of three membrane-bound receptors in close proximity which are all activated by the presence of a single TNF molecule. The TNF molecule itself appears to have a trimeric quaternary structure and, therefore, fits well with the three membrane-bound receptors. The dimeric form of the recombinant soluble TNF receptor as developed by Immunex and Synergen also takes advantage of the trimeric form of the TNF in that it blocks two of the sites and, therefore, prevents complete adhesion of the circulating TNF to the bound three-receptor system on the recipient cell membrane. A disadvantage of monoclonal antibody application in this regards is that it is specific for one antigenic region of the TNF molecule and, therefore, has no opportunity to block more than one receptor site on the circulating TNF molecule.

The safety of IL-1ra after intravenous administration has been demonstrated during the past four years in mice, rats, rabbits, dogs, primates, and humans (Wakabayashi et al., 1991; Ohlsson et al., 1990; Aiura et al. 1991; Fischer et al. 1991; Waage and Espevik, 1988; Fischer et al. 1992; Granowitz et al., 1992). In normal volunteers, IL-1ra has been demonstrated to have a half-life of approximately twenty-seven minutes after intravenous administration and the plasma clearance of IL-1ra appeared to correlate with creatine clearance (Bloedos et al., 1992). In general, a continuous IV drip is used to maintain adequate circulating levels with 2.0 mg/kg/hr being the preferred embodiment. Hence, there already exists a regimen for IL-1ra administration for humans.

In the preferred embodiment, rTNFsr is used as the cytokine antagonist. rTNFsr has been used in both Phase I and Phase II clinical trials. (Mohler, 1994) Therefore, the regimen for rTNFsr has been established for humans. Pharmokinetic studies to date indicate that 2 mg/kg body weight administered to a patient every 24 hours should obtain blood levels which are high enough to achieve near complete blockade of circulating tumor necrosis factor. The half-life of the dimeric form of rTNFsr is at or just above 26 hours in humans. This allows the use of a once-a-day dosage regimen in a preferred embodiment when appropriate.

The rTNFsr or the combination of rTNFsr and IL-1ra can be administered in combination with other drugs or singly consistent with good medical practice. The other drugs can be somatostatin or an analog (i.e., Sandostatin®) and prostaglandin inhibitors (i.e., non-steroidal, anti-inflammatory drugs such as aspirin, indomethacin, ibuprofen, etc.). Additionally, steroids or other drugs designed to suppress the immune system and other synthetic or recombinant antagonists or blockers to cytokines (e.g., soluble IL-1 receptors, soluble IL-6 receptors or others; monoclonal antibodies to IL-1, IL-6, TNF or others, etc.) can be administered. Further, nitric oxide inhibitors or antagonists, platlet activating factor antagonists, free radical scavengers or anti-oxidants, antagonists or blockers of complement, ecosinoids or their antagonists, anti-proteases and antibiotics, as appropriate, can also be administered.

The rTNFsr or combination of rTNFsr and IL-1ra is administered and dosed taking into account the clinical condition of the individual patient, the site and method of administration, scheduling of administration, and other factors known to medical practitioners. The "effective amount" for purposes herein is thus determined by such considerations as are known in the art. The amount must be effective to obtain blood levels which have been shown to be high enough to achieve near complete blockade of circulating tumor necrosis factor. Improved survival rate, more rapid recovery including decreased time in ICU and more rapid return to regular diet, or improvement or elimination of symptoms are also measurements of effective amount.

In the method of the present invention, the rTNFsr or combination of rTNFsr and IL-1ra can be administered in various ways. It should be noted that the rTNFsr or combination of rTNFsr and IL-1ra can be administered as the compound or as pharmaceutically acceptable salt and can be administered alone or in combination with pharmaceutically acceptable carriers. The compounds can be administered subcutaneously or parenterally including intravenous, intraarterial, intramuscular, intraperitoneally, and intranasal administration with intravenous the preferred method. Implants of the compounds are also useful. The patient being treated is a warm-blooded animal and, in particular, mammals including man.

It is noted that humans are treated generally longer than the mice exemplified herein which treatment has a length proportional to the length of the disease process and drug effectiveness. The components of the combination can be administered individually but a single combination dose is preferred. In general, the combination of rTNFsr and IL-1ra consists of equal parts of each component but can be adjusted so that the activity of each component provides adequate antagonism of its specific cytokine. The quantity of the combination of rTNFsr and IL-1ra to be administered will vary for the patient being treated and will vary from about 0.01 mg/kg of body weight to 100 mg/kg of body weight per day.

When administering the rTNFsr or combination of rTNFsr and IL-1ra parenterally, the rTNFsr or combination of rTNFsr and IL-1ra is formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity is maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, may be added. Prevention of the action of microorganisms may be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form are brought about by the use of agents delaying absorption, for example, aluminum monostearate and gelatin. According to the present invention, however, any vehicle, diluent, or additive used would have to be compatible with the compounds.

Sterile injectable solutions are prepared by incorporating the compounds utilized in practicing the present invention in the required amount of the appropriate solvent with various of the other ingredients, as desired.

A pharmacological formulation of the rTNFsr or combination of rTNFsr and IL-1ra is administered to the patient in an injectable formulation containing any compatible carrier, such as various vehicle, adjuvants, additives, and diluents. Alternatively, the compounds utilized in the present invention may be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

Known techniques which deliver the rTNFsr or combination of rTNFsr and IL-1ra intravenously and retain the biological activity are preferred.

In one preferred embodiment, the rTNFsr or combination of rTNFsr and IL-1ra is administered initially by intravenous injection to bring blood levels of rTNFsr or combination of rTNFsr and IL-1ra to a suitable level (bolus). The patient's rTNFsr or combination of rTNFsr and IL-1ra levels are then maintained by a continuous drip for the IL-1ra and/or daily injections for the rTNFsr, although other forms of administration, dependent upon the patient's condition, as indicated above, can be used. The quantity of rTNFsr to be administered will vary for the patient being treated and will vary from about 0.01 mg/kg of body weight to 100 mg/kg of body weight per day and preferably will be from 0.5 mg/kg to 10 mg/kg per day.

IL-1, IL-6, and TNF-$\alpha$ are elevated during all acute pancreatitis models which have examined these mediators to date, including: (1) caerulein in the mouse (Norman et al., 1994); (2) caerulein in the rat (Guice et al., 1991; Norman et al., 1994; and Grewal et al., 1994); (3) caerulein and ethanol in the rat (Normal et al., 1994); (4) retrograde infusion of bile acid into the pancreatic duct (Dolan et al., 1994); (5) CDE diet in the mouse (Norman et al., 1994) and (6) microvascular ischemia (Formela et al., 1994) (not intended to be a complete listing).

Applicant has recently observed an increase in the production and release of inflammatory cytokines when iv alcohol is added to a model of caerulein-induced pancreatitis in the rat. This provides support to the toxic metabolic hypothesis first proposed by Noronha et al. (1988) suggesting that ethanol has a direct injurious effect on the pancreas, leading ultimately to pathophysiologic changes culminating in pancreatitis. The constancy of cytokine elevation within multiple animal models adds further evidence that these mediators play a significant role in the pathogenesis of this disease and allows for the study of this process in different models.

The above discussion provides a factual basis for the use of cytokine cascade blockers. The methods used with and the utility of the present invention can be shown by the following examples.

EXAMPLES

GENERAL METHODS

Animals

Female NIH Swiss mice obtained from Harlan and maintained in the Animal Housing Unit of the University of South Florida. All experiments were conducted with the prior approval of the Laboratory Animal Medicine Ethics Committee at the University of South Florida College of Medicine.

Therapeutics

The IL-1ra used in this study is produced in *E. coli* by Synergen Corporation (Boulder, Colo.) by utilizing recombinant DNA technology and is identical to the non-glycosylated human form of human IL-1ra except for the addition of one terminal methionine amino acid.

The recombinant TNF soluble receptor (rTNFsr) used in this study is produced in *E. coli* by Synergen Corporation (Boulder, Colo.) by utilizing recombinant DNA technology and is identical to the non-glycosylated human form of human IL-1ra except that a dimer of the receptor is formed through an ethylene glycol linkage. Additionally rTNFsr produced by Immunonex Corp. (Seattle, Wash.) can also be used.

The dimer form of the receptor (rTNFsr) has the advantage of increasing the affinity ten-fold and increasing the half-life to approximately 27 hours, thereby allowing once-a-day doses.

CDE Diet

A lethal form of acute hemorrhagic necrotizing pancreatitis was induced in young female NIH Swiss mice. The young female NIH Swiss mice (4–5 weeks, 15.5±0.4 grams) were fasted for 12 hours and then fed a choline deficient diet (Harlan Teklad, Madison, Wis.), supplemented with 0.5% ethionine (Sigma, St. Louis, Mo.) for 72 hours (CDE diet). The experimental diet was replaced every six hours to assure equal exposure by all animals and to maintain sanitary conditions. At the end of the 72 hour period, the experimental diet was replaced with regular chow. Water was allowed ad libitum at all times. The animals were randomly assigned to one of three treatment groups of Control, early treatment or late treatment. Mortality was determined for each group every six hours for 10 days.

Histological Grading

Histologic grading of pancreas tissue sections for necrosis, inflammation, vacuolization and edema was undertaken in a blinded fashion. Each pancreas was fixed, stained, and graded histologically in a blinded fashion for interstitial edema, granulocyte infiltration, acinar vacuolization, and acinar cell necrosis as described previously (Tani et al., 1987; Grewel et al., 1994); (Guice et al., 1991; Zhu et al., 1991).

Histologic slides were prepared as is known in the art after rapid excision, the determination of wet weight and subsequent fixation in 10% formalin. The tissues were paraffin embedded as is known in the art and then stained with Hematoxylin and Eosin in a standard fashion. These slides were examined and graded in a blinded fashion by a board certified pathologist. All specimens were graded (range 0 to 4, normal control and severe untreated pancreatitis, respectively) for degree of edema, necrosis, vacuolization, and inflammatory cell infiltrate.

Serum levels of amylase, lipase, IL-6, and TNF

Serum amylase and lipase levels were determined using a Kodak Ektachem 700 automated analyzer which had been standardized for these murine proteins. All samples were assayed in triplicate and averaged.

Serum concentrations of IL-1, IL-6, TNF-α, and IL-1ra were measured in triplicate using ELISA methodology. All specimens were run in triplicate. Briefly, 96-well microtiter plates (Corning, N.Y.) were prepared by coating with the appropriate primary capture monoclonal antibody overnight (rat anti-murine TNF-α and IL-1 from Endogen (Boston, Mass.); rat anti-murine IL-6 from PharMingen (San Diego, Calif.); rat anti-human IL-1ra from Synergen (Boulder, Colo.). A standard curve was prepared using the appropriate recombinant cytokines run in conjunction with the serum samples. Following the initial incubation, the plates were washed and then incubated with a biotinylated monoclonal detection antibody. Following a second wash, avidin-peroxidase was added and detected using ABTS as substrate. Optical density was determined at 405 nm using a Bio-Tek EL 309 automated plate reader and analyzed using an Immunosoft software package (Dynatech Laboratories, Chantilly, Va.).

Commercially available ELISA kits (Genzyme Corp., Boston, Mass.; R&D System, Minneapolis, Minn.) are also available.

EXAMPLE 1

TREATMENT WITH IL-1ra

Protocol

Control—received 100 μl normal saline (NS) intraperitoneal (IP) every 6 hours for 5 days;

IL-1ra early-beginning at time 0 received recombinant IL-1ra (Synergen) 15 mg/kg IP every 6 hour for 5 days beginning at time 0;

IL-1ra late-beginning 1.5 days after introduction of the CDE diet received IL-1ra 15 mg/kg IP every 6 hours for 3.5 days.

For determination of mechanisms of action, a parallel experiment (PE) was conducted simultaneously with a minimum of 29 animals per group. Nine animals from each PE group were sacrificed at time 0, and four animals from each group on day 1, 2, 3, 4 and 6 with comparisons made of serum amylase, lipase, IL-1, IL-6, TNF-α, and IL-1ra in addition to pancreatic wet weights and blind histopathologic grading, therefore allowing comparisons between dosage, serum level, systemic cytokine response, and degree of pancreatic damage.

Results

Figure 1:
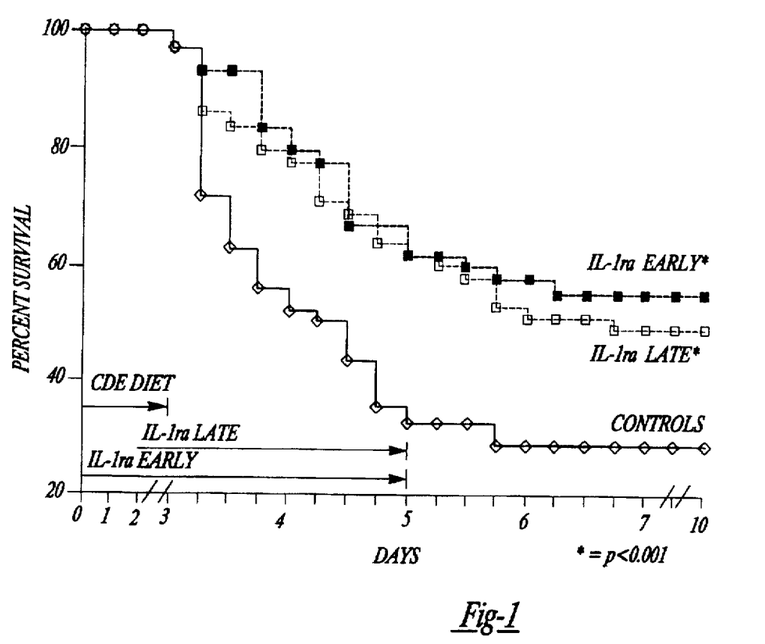
FIG. 1 is a graph of the percent survival of control (●), IL-1ra early treatment (■) and IL-1ra late (□) treated mice.

The 72 hour CDE diet resulted in severe hemorrhagic necrotizing pancreatitis with a mortality rate of 73 percent in control animals (FIG. 1). Early and late administration of IL-1ra decreased mortality to 44 percent and 51 percent, respectively (FIG. 1, <0.001, chi square). Although prophylactic IL-1ra administration resulted in fewer deaths than delayed therapy, the difference was not statistically significant (p=0.39).

Figure 2A:
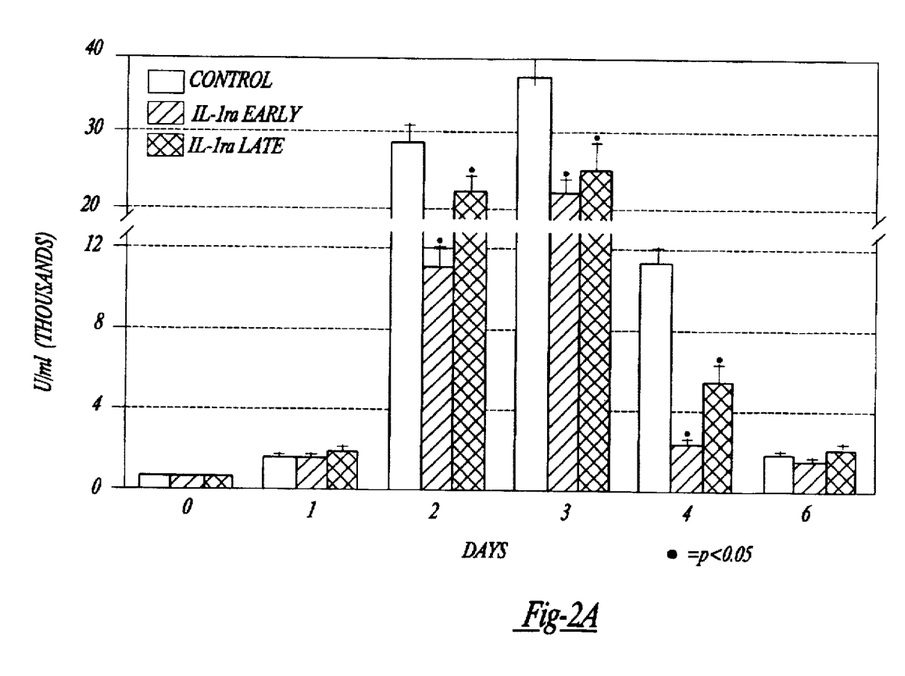
FIGS. 2A and 2B are bar graphs of the elevation of serum amylase (FIG. 2A) and lipase (FIG. 2B) following induction of severe pancreatitis in Control (cross-hatched), IL-1ra early treatment (stippled) and IL-1ra late treatment (diagonal lines) mice, (*=p<0.05)
Figure 2B:
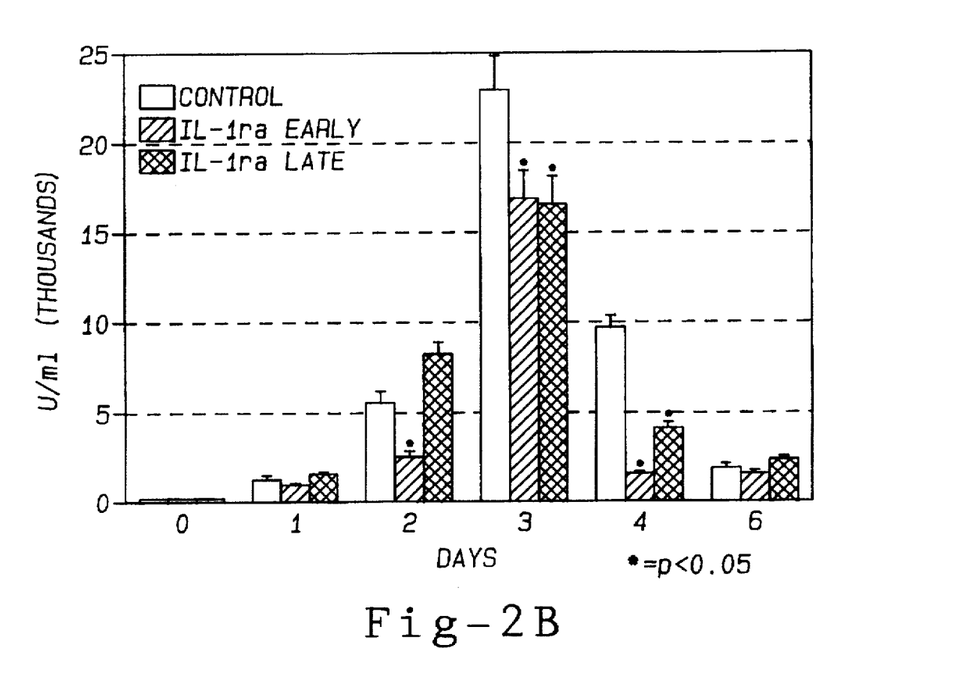

The concentrations of amylase and lipase in the serum of Control animals increased with the development of pancreatitis, peaking on day 3 at over 25,000 u/ml and 21,000 u/ml, respectively (both p<0.0001 compared to time 0). Administration of IL-1ra significantly attenuated the rise in both of these enzymes regardless of the timing of therapy (FIG. 2, A and B; all p<0.05). The IL-1ra Late treatment group closely paralleled the Control group in this respect until after therapy had begun.

Figure 3:
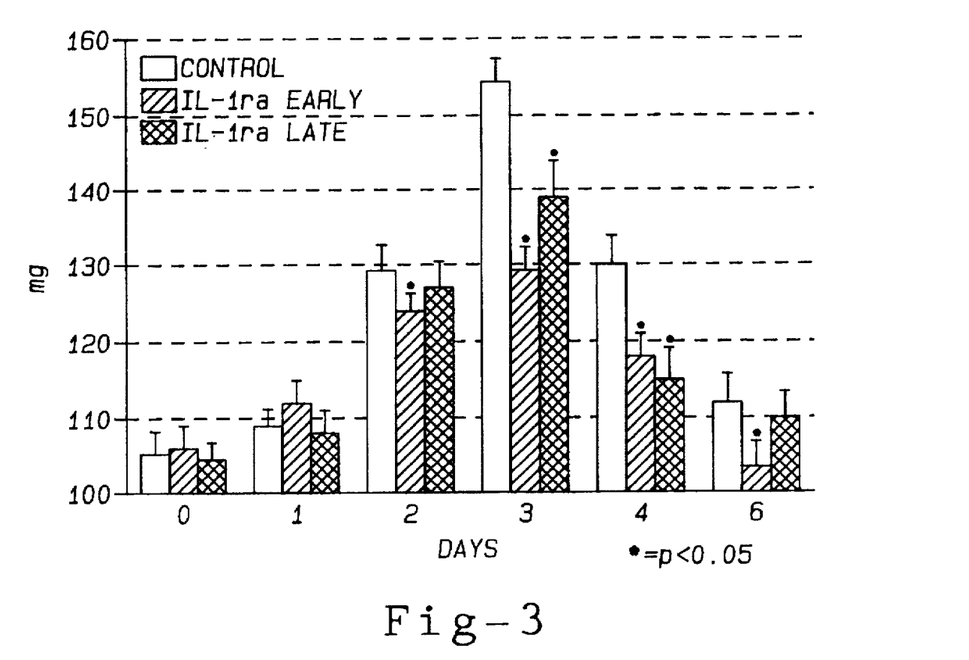
FIG. 3 is a bar graph of the pancreatic wet weight of Control (cross-hatched), IL-1ra early treatment (stippled) and IL-1ra late treatment (diagonal lines) mice, (*=p<0.05)

Pancreatic wet weight within the Control group nearly doubled following the induction of pancreatitis as shown in FIG. 3 (p<0.01 compared to baseline). Both early and late administration of IL-1ra attenuated this increase (p<0.05 compared to Control), with prophylactic therapy being slightly more efficacious than delayed.

Figure 4A:
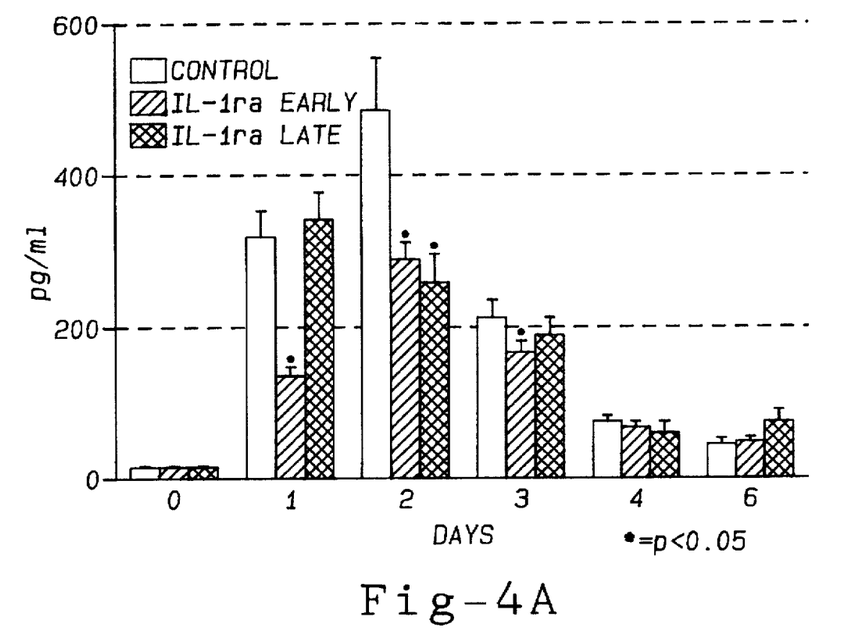
FIGS. 4A, 4B and 4C are bar graphs of serum cytokine concentration during the course of severe pancreatitis, with (FIG. 4A) IL-1, (FIG. 4B) IL-6, and (FIG. 4C) TNF-α in Control (cross-hatched), IL-1ra early treatment (stippled) and IL-1ra late treatment (diagonal lines) mice, (*=p<0.05 compared to Control)
Figure 4B:
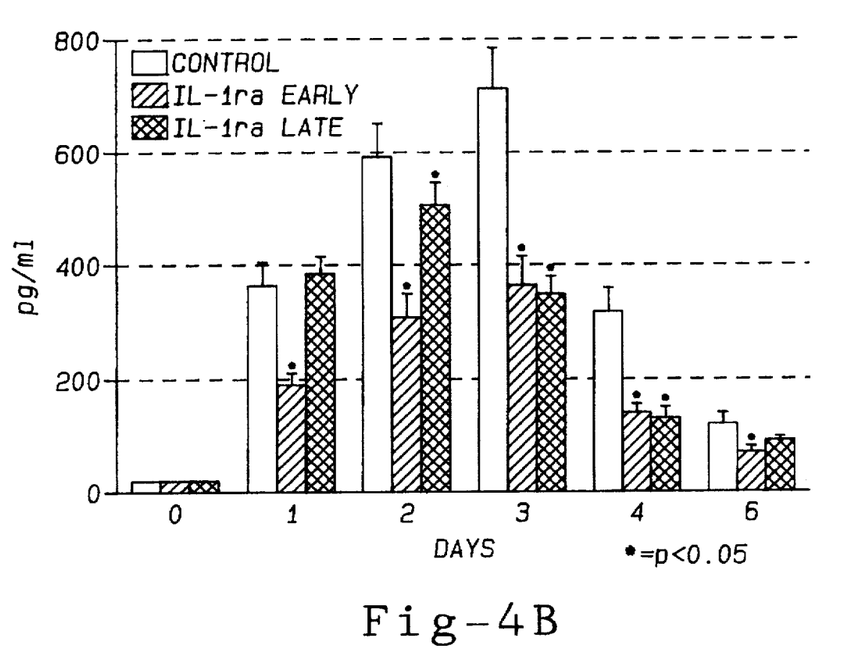
Figure 4C:
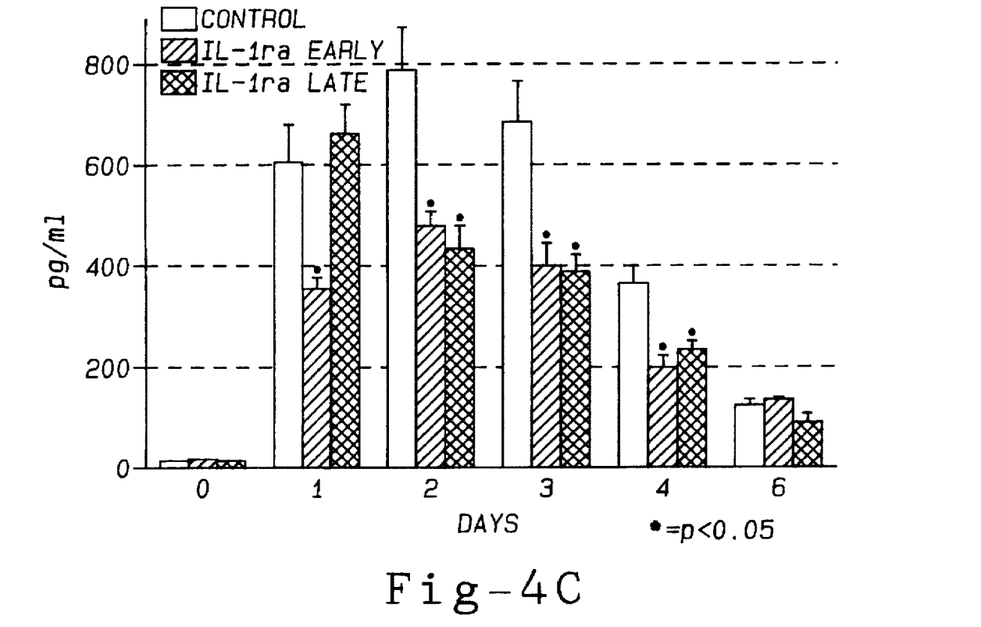
Figure 5:
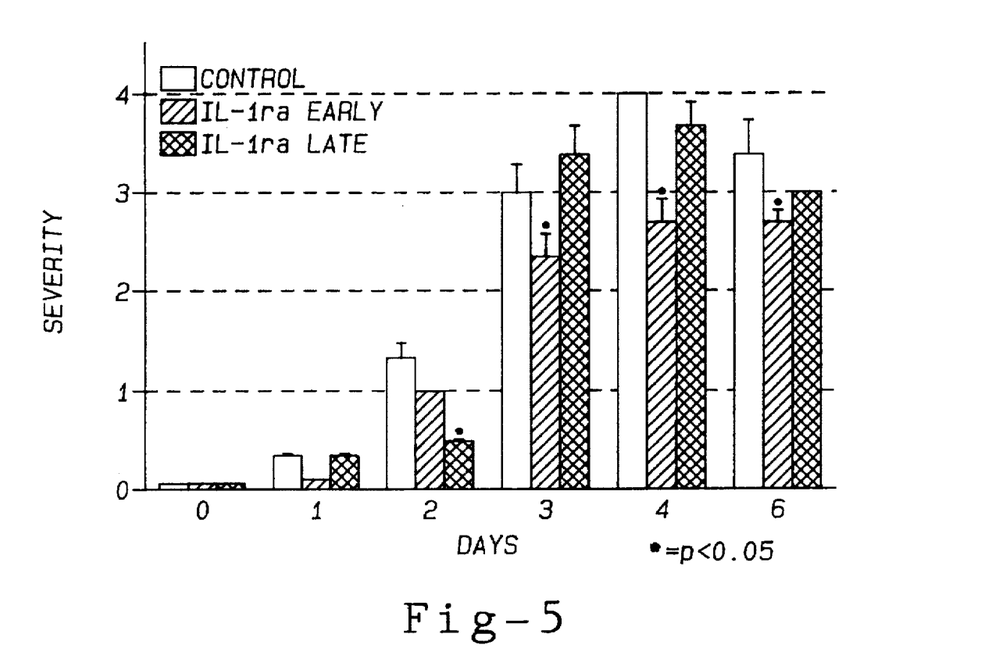
FIG. 5 is a bar graph of the severity of necrosis of Control (cross-hatched), IL-1ra early (stippled) and IL-1ra late (diagonal lines) treated mice.
Figure 6:
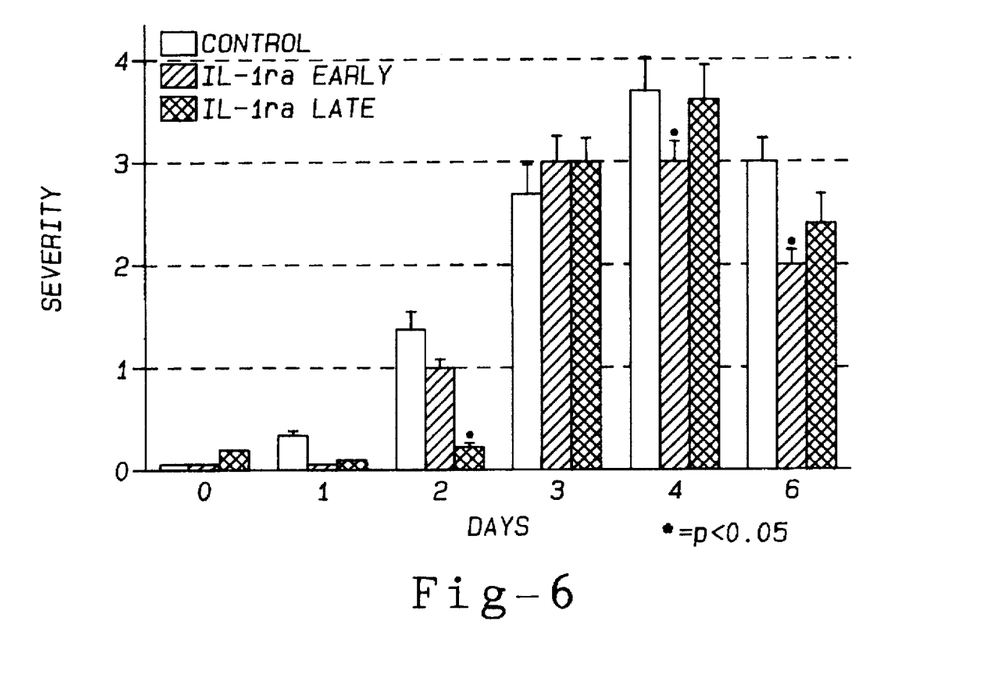
FIG. 6 is a bar graph of the severity of inflammation of Control (cross-hatched), IL-1ra early (stippled) and IL-1ra late (diagonal lines) treated mice.
Figure 7:
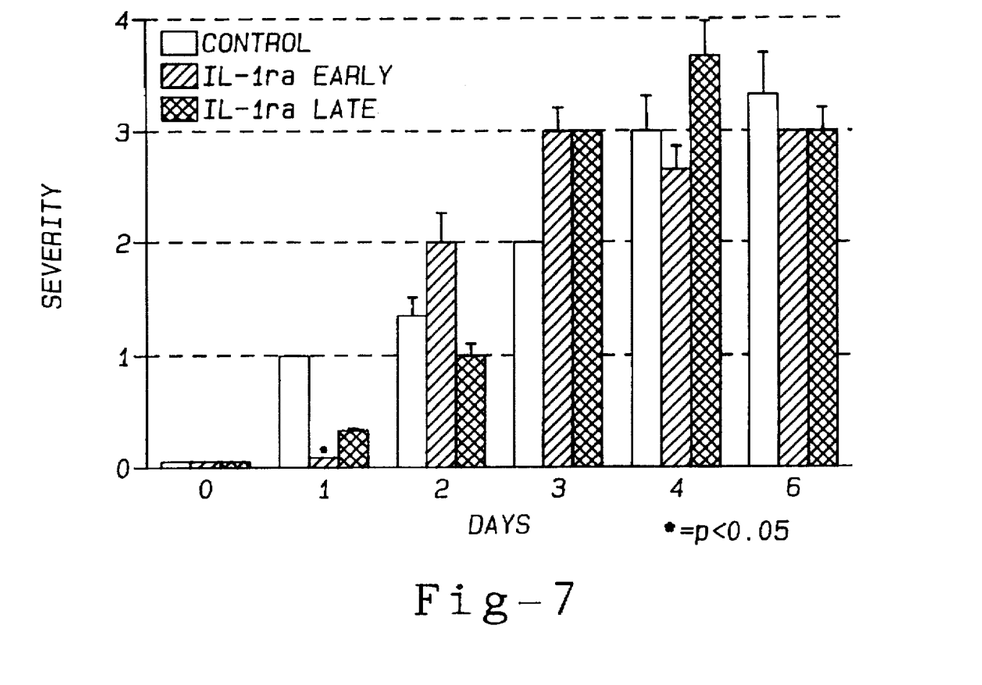
FIG. 7 is a bar graph of the severity of vacuolization of Control (cross-hatched), IL-1ra early (stippled) and IL-1ra late (diagonal lines) treated mice.
Figure 8:
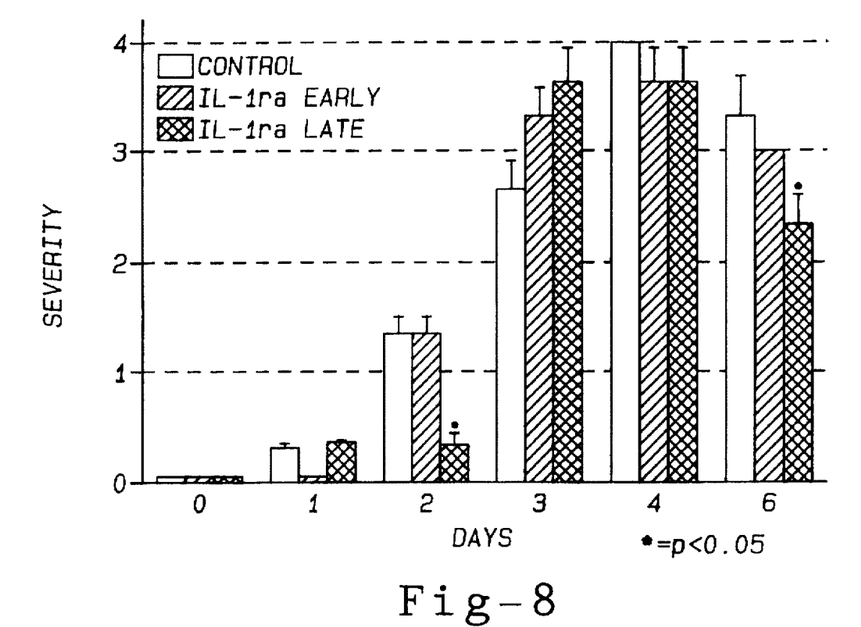
FIG. 8 is a bar graph of the severity of edema of Control (cross-hatched), IL-1ra early (stippled) and IL-1ra late (diagonal lines) treated mice.

All animals experienced a rapid and sustained elevation of the inflammatory cytokines IL-1, IL-6, and TNF-α concomitant with the development of acute pancreatitis (all p<0.0001 compared to time 0). Both early and late treatment with IL-1ra significantly decreased the appearance of all three of these mediators at all time points once therapy was instituted (FIG. 4, A–C; all p<0.05).

The induction of pancreatitis was associated with a variable intrinsic production of IL-1ra in Control animals (mean 0.120±0.028 ng/ml). Those animals receiving exogenous IL-1ra maintained levels significantly higher (mean 33±6.2 ng/ml) once therapy was instituted, and lasting through day 5 (p<0.05 compared to Control).

Figure 9:
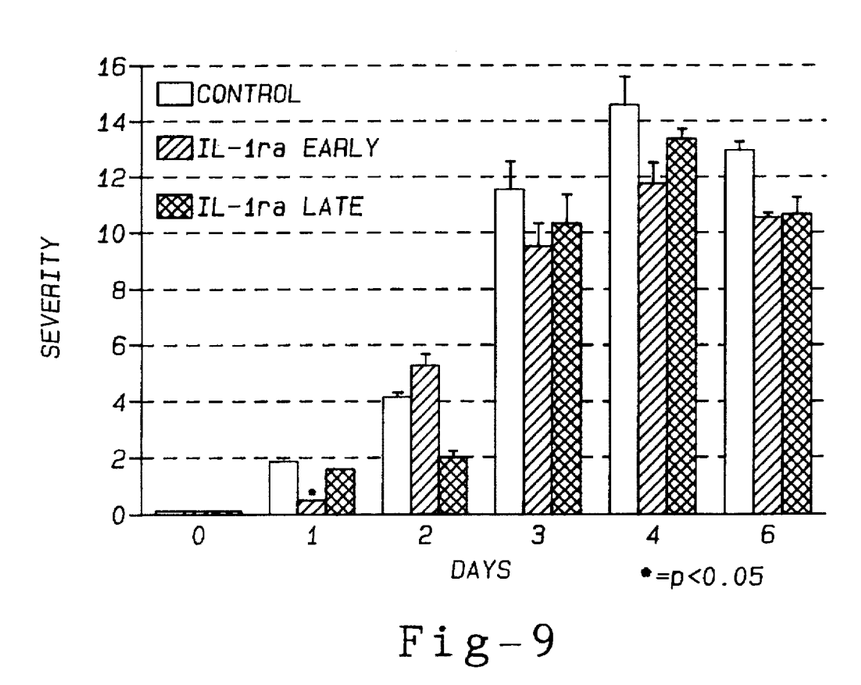
FIG. 9 is a bar graph of combined blind histologic assessment of necrosis, inflammation, edema, and vacuolization are combined to demonstrate the overall histologic severity of pancreatitis, in Control (cross-hatched), IL-1ra early treatment (stippled) and IL-1ra late treatment (diagonal lines) mice, (*=p<0.05)

Blind histologic grading of pancreata from all groups revealed a severe hemorrhagic necrotizing pancreatitis, peaking 72 hours after first CDE diet exposure as summarized in Table 1 and FIGS. 5–8. Vacuolization was not changed by cytokine antagonism. The degree of edema and inflammatory cell infiltrate was decreased at nearly all time points in those animals receiving IL-1ra, however, this reached statistical significance in only a few instances. Necrosis, on the other hand, was consistently improved by IL-1ra therapy, showing statistical differences in both groups independent of when antagonism was initiated. When the scores from all four determinants of severity are combined to examine the overall blind histologic assessment of pancreatitis severity, the protective effects of IL-1ra administration becomes evident and shown in FIG. 9.

TABLE 1

Maximal Severity of Blind Pancreatic Histology.

| | Edema | Necrosis | Vacuolization | Inflammation |
|---|---|---|---|---|
| Saline controls | 0 | 0 | 0 | 0 |
| Severe pancreatitis | 4.0 ± 0.0 | 4.0 ± 0.0 | 3.0 ± 0.2 | 3.7 ± 0.2 |
| IL-1ra-Early | 3.6 ± 0.1 | 2.0 ± 0.1* | 2.8 ± 0.1 | 3.0 ± 0.0* |
| IL-1ra-Late | 3.3 ± 0.0* | 3.0 ± 0.0* | 3.3 ± 0.2 | 3.5 ± 0.1 |

Histologic examination of the lungs from each group revealed an inflammatory cell infiltrate progressive with the severity of pancreatitis, with maximal numbers reached on days 3 and 4 (mean 12.1±2.1 per hpf). Those animals receiving IL-1ra early in the course of pancreatitis demonstrated a decrease in the overall number of inflammatory cells infiltrating the lungs (5.7±1.4, p<0.05 compared to Control). Delayed therapy did not show a similar effect (11.8±1.8, p=0.79 compared to Control). The temporal relationship of this process to the severity of pancreatitis was not effected by IL-1 antagonism. No other pancreatitis induced pulmonary histologic abnormalities could be quantitated in any group as is typical for this model.

Discussion

The decrease in overall mortality following both prophylactic and delayed administration of IL-1ra became evident early in the study and continued through study completion when the pancreatitis had resolved. There was no significant difference in the reduction of mortality seen in the prophylactic and delayed therapy groups. This is notable since delayed therapy was instituted 36 hours after first exposure to the experimental diet at which time there was histologic and biochemical evidence of severe pancreatitis concomitant with significant elevations in circulating cytokines.

The mechanism for the dramatic survival benefits provided by proximal cytokine antagonism appears multifactorial. Intrinsic pancreatic damage was significantly decreased following IL-1 blockade as measured by wet weight and pancreatic enzyme release, the latter most likely representing decreased acinar cell destruction and lysis. Histologic examination confirmed attenuated necrosis in all animals receiving the antagonist. The reasons for the IL-1ra induced pancreatic protection is unclear, but may be due to antagonism of the direct actions of IL-1 on the acinar cells or may be the secondary attenuation of IL-6 and TNF-α production. Both IL-6 and TNF-α are well known as simulators of protein synthesis and direct cellular toxicity, but like IL-1, their precise effects on pancreatic acinar, ductal, or islet cells are not well established. Indirectly, decreased levels as well as direct antagonism of these cytokines may prevent or inhibit the attraction and migration of activated leukocytes into the damaged gland and thereby attenuate the intra-pancreatic inflammatory process in a broader sense. This has been demonstrated by applicant's laboratory previously utilizing another model of acute pancreatitis (Norman et al., 1994b)

The current study demonstrates that the CDE diet-induced model of acute pancreatitis is associated with activation of the inflammatory cytokine cascade similar to that shown in both alcoholic and biliary pancreatitis in humans and is consistent with all previously studied animal models of this disease. Exposure to the CDE diet produced a severe hemorrhagic necrotizing pancreatitis which takes approximately three days to reach its maximal histologic intensity. Peak levels of the inflammatory cytokines were reached somewhat earlier, however, as has been demonstrated during pancreatitis induced by supramaximal stimulation with the cholecystokinin analog caerulein (Norman et al., 1994b).

and in clinical pancreatitis as well. The administration of IL-1ra was associated with a down regulation of the inflammatory cytokine cascade as evidenced by a dramatic decrease in serum IL-1, IL-6, and TNF-α. This is consistent with the proximal position IL-1 maintains within the cytokine cascade whereby it may induce the production and secretion of other cytokines including IL-6 and TNF-α, as well as itself (Openheim et al., 1993; Aiura et al., 1991) The attenuation of the expected rise in these mediators has been shown previously following the administration of IL-1ra during sepsis (Granowitz et al, 1992b) and during caerulein-induced pancreatitis (Norman et al, Surgery, 1994b). Importantly, an effective dose of the antagonist was able to attenuate subsequent production of IL-6 and TNF-α when given in a delayed fashion at a time when elevated levels of the mediators were already present in the serum.

EXAMPLE 2

TREATMENT WITH rTNFsr

Tumor necrosis factor-α (TNF) is known to be produced during acute pancreatitis and has been implicated as a central mediator in the progression of local and systemic pathology associated with this disease. To determine if inhibition of this cytokine would lead to survival benefits, a recombinant dimeric form of the soluble TNF receptor (rTNFsr) was evaluated in a lethal model of acute hemorrhagic necrotizing pancreatitis.

Protocol

Pancreatitis was induced in female Swiss mice by feeding a choline deficient, ethionine supplemented (0.05%) (CDE) diet for 72 hours. For comparison of mortality rates, the animals were divided into three groups of 55:

Control: received 2 mg/kg bovine serum albumin IP every day for 5 days;

rTNFsr early: received rTNFsr 2 mg/kg IP every day for 5 days beginning at time 0;

rTNFsr late: received IP albumin for 1.5 days followed by rTNFsr for 3.5 days.

For determination of mechanisms of action, a parallel experiment was conducted with a minimum of 32 animals per group. Randomly selected animals were sacrificed on days 0, 1, 2, 3, 4, and 6 with comparisons made of serum amylase, lipase, IL-6, and TNF, in addition to pancreatic wet weight and blind histophalogic grading.

Results

Figure 10:
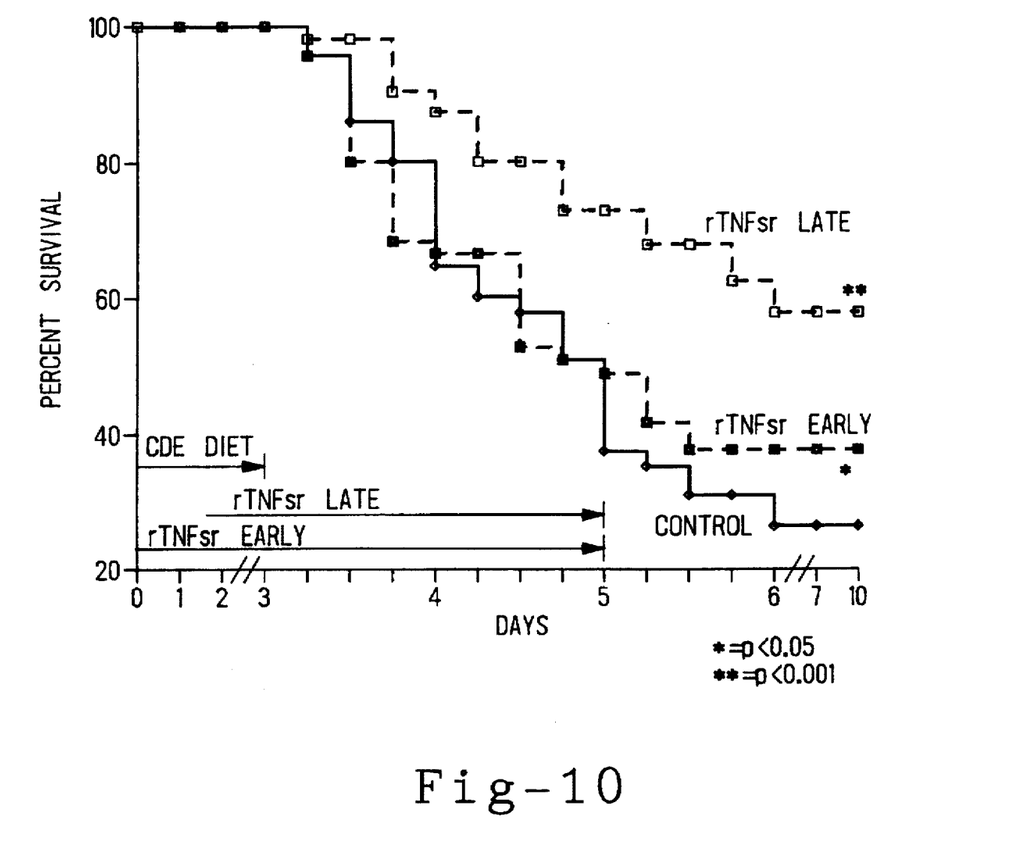
FIG. 10 is a graph of the percent survival of Control (●), rTNFsr early treatment (■) and rTNFsr late (58) treated mice.

The 72 hour CDE diet resulted in severe pancreatitis with a 10-day mortality rate of 74% in Control animals (FIG. 10). Early and Late administration of rTNFsr decreased mortality to 65% and 42%, respectively (Early p<0.05 vs. Control; Late p<0.001 vs. control. Fisher's Exact). Delaying therapy until pancreatitis had developed increased survival an additional 23% (p<0.05 Late vs. Early).

All animals developed a rapid and equivalent elevation of serum TNF and IL-6 independent of TNF blockade. Pancreatic wet weight increased significantly for all three groups, with pancreata from both rTNFsr treated groups returning to normal weight two days sooner than Control (Early and Late p<0.05). Blind histologic grading revealed significantly less necrosis in both rTNFsr groups on days 3 through 5 (Early and Late less than control, p<0.05).

Discussion

Blockade of pancreatitis-induced TNF secretion yields significant histologic and survival benefits. Delaying antagonism of TNF until after pancreatitis-associated cytokines are elevated appears to be significantly more efficacious.

Early or late blockade of the cytokine cascade with either IL-1ra or rTNFsr significantly decreases the expected mortality of severe acute pancreatitis. This is the first time that delayed therapy has been shown to significantly effect outcome in this disease. The present invention also allows the identification of patients with elevated levels of these cytokines (discussed earlier), who would be the appropriate candidates for cytokine antagonists.

Throughout this application, various publications and patents are referenced. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Aiura K, Gelfand J. A., Wakabayashi G., et al: Interleukin-1 receptor antagonist blocks hypotension in a rabbit model of gram-positive septic shock. Cytokine 4:498, 1991.

Bloedos D. C., Stiles D. M., Beshore A. L., et al: Intravenous disposition of interleukin-1 receptor antagonist in healthy volunteers. Amer Soc Clin Pharmacology and Therapeutics March, 1992. Orlando, Fla. (Abstract)

Cioffi W. C., Burleson D. G., Pruit B. A.: Leukocyte responses to injury. Arch Surg 128:1235–41, 1993.

Coticchia J. M., Lessler M. J. A., Carey L. C., et al: Peritoneal fluid in human acute pancreatitis blocks hepatic mitochondrial respiration. Surgery 100(5):850–855, 1986.

Deitch E. A.: Multiple organ failure. Ann Surg 216:117–134 1992.

Dinarello C. A., Gelfand J. A., Wolf S. M.: Anticytokine strategies in treatment of systemic inflammatory response syndrome. JAMA 269:1829–1834, 1993.

Dolan S., Campbell G., Rowlands B. J.: Biphasic tumor necrosis factor release in experimental acute pancreatitis. Gut 35:A575, 1994. (Abstract)

Ellison E. C., Pappas T. N., Johnson J. A., et al: Demonstration and characterization of the hemoconcentrating effect of ascitic fluid that accumulates during hemorrhagic pancreatitis. J Surg Research 30:241–248, 1981.

Fischer E., Marano M. A., Van Zee K. J., et al: Interleukin-1 receptor blockade improves survival and hemodynamic performance in *Escherichia coli* septic shock, but never fails to alter host responses to sublethal endotoxemia. J Clin invest 89:1551, 1992.

Fischer E., Marano M. A., Barber A., et al: A comparison between the effects of interleukin-1 administration and sublethal endotoxemia in primates. Am J Physiol 261:R442, 1991.

Formela L. J., Mclaughlin P. J., Flanagan B. F., et al: Demonstration of tumor necrosis factor in pancreatic acinar cells by in situ hybridisation in a model of acute pancreatitis. Gut 35:A575, 1994 (Abstract)

Granowitz E. V., Porat R., Mier J. W., et al: Pharmacokinetics, safety and immunomodulatory effects of human recombinant interleukin-1 receptor antagonist in healthy humans. Cytokine 4:353, 1992.

Granowitz E. V., Clark B. D., Vannier E., et al: Effect of Interleukin-1 (IL-1) blockade on cytokine synthesis: I. IL-1 receptor antagonist inhibits IL-1-induced cytokine synthesis and blocks the binding of IL-1 to its type II receptor on human monocytes. Blood 79:2356–2363, 1992b.

Grewal H. P., Mohey el Din A., Gaber L., et al: Amelioration of physiologic and biochemical changes of acute pancreatitis using an anti-TNF-α polyclonal antibody. Amer J Surg 167:214–19, 1994a.

Grewal H. P., Kotb M., Mohey el Din A., et al: induction of tumor necrosis factor in severe acute pancreatitis and its subsequent reduction after hepatic passage. 115(2):213–221, 1994b.

Grewal H. P., Hughes C. B., Mohey el Din A., et al: Anti-TNF therapy improves survival and ameliorates the pathophysiologic sequelae in acute pancreatitis in the rat. Gastroenterology 106:163, 1994.

Gross V., Leser H.-G., Heinisch A., et al: Inflammatory mediators and cytokines-new aspects of pathophysiology and assessment of severity of acute pancreatitis?. Hepato-Gastroenterol 40:522–529, 1993.

Guice K. S., Oldham K. T., Remick D. G., et al: Anti-tumor necrosis factor antibody augments edema formation in caerulein-induced pancreatitis. J Surg Res 51:495–499, 1991.

Guice K. S., Oldham K. T., Caty M. G., et al: Neutrophil-dependent, oxygen-radical mediated lung injury associated with acute pancreatitis. Ann Surg 210:740–747, 1989.

Heath, D. I., Cruickshank A., Gudgeon M., et al: Role of interleukin-6 in mediating the acute phase protein response and potential as an early means of severity assessment in acute pancreatitis. Pancreas 66:41–45, 1993.

Imrie C. W., Whyte A. S.: A prospective study of acute pancreatitis. Br J Surg 62:490–494, 1975.

Jacobs M. L., Daggett W. M., et al: Acute pancreatitis: Analysis of factors influencing survival. Ann Surg 185:43–51, 1977.

Kelly D. M., McEntree G. P., McGeeney K. F. et al: Microvasculature of the pancreas, liver, and kidney in caerulein-induced pancreatitis. Arch Sug 128:293–295, 1993.

Kotb M., Mohey A., Ohman M. et al: TNF production during acute pancreatitis is not endotoxin mediated. Proc. 28th Annual Meeting of Pancreas Club, 1994.

Larsen G. L., and Henson P. M.: Mediators of inflammation. Ann. Rev. Immunol 1:335–359, 1983.

Leach S. D., Gorelick S., Modlin I. M.: New perspectives on acute pancreatitis. Scan J Gastroenterol 27 Suppl 192:29–38, 1992.

Lowry S. F.: Cytokine mediators of immunity and inflammation. Arch Surg 128:1235–1241, 1993.

McKay C., Gallagher G., Baxter J. N., et al: Systemic complications in acute pancreatitis are associated with increased monocyte cytokine release. Gut 35:A575, 1994 (Abstract).

Michie H. R., Wilmore D. W.: Sepsis, signals, and surgical sequelae. Arch Surg 125:531–536, 1990.

Mohler, K. M.: The use of soluble TNF receptors as inhibitors of inflammation. Proceedings of regulation of cytokine activity for therapeutic development—Control of inflammation, growth and differentiation. Mar. 3, 1994, Washington, D.C. (Abstract).

Murayama K. M., Drew J. B., and Joehl R. J.: Does somatostatin analogue prevent experimental acute pancreatitis? Arch Surg 125:1570–1572, 1990.

Norman J., Franz M.: Acute phase cytokines during experimental acute pancreatitis. Cytokine, 1994 (in press)

Norman J., Franz M., Messina J., et al: intrinsic production of pro-inflammatory cytokines by pancreas during acute pancreatitis. Surg Forum XLV:191–194, 1994a.

Norman J., Messina J., Franz M., et al: Interleukin-1 receptor antagonist decreases severity of experimental acute pancreatitis. Surgery. 1994b (in press).

Norman J., Franz M., Messina J., et al: Decreased severity of experimental acute pancreatitis by pre or post treatment with Interleukin-1 receptor antagonist. 28th Annual Meeting. Pancreas Club, Inc. (New Orleans, La.) May 1994c; p. 23. (Abstract)

Noronha M., Salgadinho A., Ferreira de Almeida M. J., et al: Alcohol and the pancreas. I. Clinical associations and histophatholgy of minimal pancreatic inflammation. Am J Gastroenterol. 3:9–18, 1988.

Ohlsson K., Bjork P., Bergenfeldt M., et al: An interleukin-1 receptor antagonist reduces mortality from endotoxin shock. Nature 348:550, 1990.

Okusawa S., Gelfand J. A., Ikejima T., et al: Interleukin-1 induces a shock-like state in rabbits. Synergism with tumor necrosis factor and the effect of cyclooxygenase inhibition. J Clin invest 81:1162, 1988.

Oppenheim J. J., Rossia J. L., Gearing A. J. H.: Clinical applications of cytokines; Role in pathogenesis diagnosis and therapy (Oxford University Press, New York, N.Y.) pp. 1–27, 1993.

Pappas T. N., Lessler M. A., Ellison E. C., et al: Pancreatitis-associated ascitic fluid: Effect on oxygen consumption of liver cells. Soc Exp Biol Med 187:565–573, 1978.

Physicians' Desk Reference®: pp. 1654–1658, 1994.

Ranson J. H. C., Spencer F. C.: Role of peritoneal lavage in severe acute pancreatitis. Ann Surg 187:565–573, 1978.

Rodgers R. E., Carey L. V.: Peritoneal lavage in experimental pancreatitis in dogs. Amer J Surg 111:792–794, 1966.

Schoenberg M. H., Büchler M., Beger H. G.: The role of oxygen radicals in experimental acute pancreatitis. Free Radical Biology & Medicine 12:515–522, 1992.

Spillenaar Bilgen E. J., Marquet R. L., Baumgartner D., et al: Attempts to reduce post-transplant pancreatitis in rats and dogs with the somatostatin analogue SMS 201–995. Transplant Proceed 21:2829–2830, 1989.

Steer M. L.: How and where does acute pancreatitis begin? Arch Surg 127:1350–1353, 1992.

Steinberg W., Tenner S.: Acute pancreatitis. N Eng J Med 330:1198–1220, 1994.

Stone H. H., Fabian T. C.: Peritoneal dialysis in treatment of acute alcoholic pancreatitis. Surg Gynecol Obstet 150:878–882, 1980.

Tani S., Otsuki M., Itoh H., et al: Histologic and biochemical alterations in experimental acute pancreatitis induced by supramaximal caerulein stimulation. Intl J Pancreatology 2:337–348, 1987.

Takeyama Y., Saitch Y.: Possible involvement of peritoneal macrophage activation in remote organ failure with acute pancreatitis. Meeting of the Society of University Surgeons. February, 1994. Jackson, Miss. (Abstract #106).

Torab F. C., Berger D., Uhl W., et al: Clinical significance of endotoxin Interleukins-6 and transferrin during acute pancreatitis. Meeting of the Society of University Surgeons, February, 1994. Jackson, Miss. (Abstract #116).

Van Ooijen B., Kort W. J., Tinga C. J., et al: Significance of thromboxane $A_2$ and Prostaglandin $I_2$ in acute necrotizing pancreatitis in rats. Digestive Disease and Sciences 35:1078–1084, 1990.

Waage A., Espevik T.: Interleukin-1 potentiates the lethal effect of tumor necrosis factor/cachectic in mice. J Exp Med 167:1987, 1988.

Wakabayashi G., Gelfand J. A., Burke J. F., et al: A specific receptor antagonist for interleukin-1 prevents *E. coli* induced shock in rabbits. FASEB 5:338, 1991.

Zhu Z. H., Holt S., El-Lbishi M. S., et al: A somatostatin analogue is protective against retrograde bile salt-induced pancreatitis in the rat. Pancreas 6:609–613, 1991.

What is claimed is:

1. A method for treating a person with acute pancreatitis which comprises administering an effective amount of a tumor necrosis factor (TNF) antagonist or a pharmaceutically acceptable salt.

2. The method of claim 1 wherein the tumor necrosis factor antagonist is suspended in an acceptable carrier.

3. The method of claim 1 wherein the tumor necrosis factor antagonist is a tumor necrosis factor soluble receptor (TNFsr) or a pharmaceutically acceptable salt.

4. The method of claim 3 wherein the tumor necrosis factor soluble receptor is a recombinant tumor necrosis factor soluble receptor (rTNFsr).

5. The method of claim 4 wherein the rTNFsr is in dimeric form.

6. The method of claim 4 wherein the effective amount of rTNFsr administered is from 100 ng/kg body weight to 100 mg/kg body weight of the patient per day.

7. The method of claim 4 wherein the effective amount of rTNFsr is administered initially by an intravenous injection to bring blood levels of rTNFsr to a suitable level after which the patients rTNFsr levels are maintained for as long as clinically indicated by either repeated daily injections or by continuous infusions.

8. The method of claim 7 wherein the rTNFsr is administered (a) intravenously as a loading dose of 2–5 mg/kg body weight in a total volume of 10 ml followed by (b) a daily intravenous injection of 2–5 mg/kg body weight in a total volume of 10 ml, or (c) a continuous infusion which will allow sufficient levels of rTNFsr to be maintained (approximately 0.5 mg/kg/hr).

9. A method for treating a person with acute pancreatitis which comprises co-administering an effective amount of a combination of a tumor necrosis factor (TNF) antagonist and Interleukin-1 receptor antagonist (IL-1ra) or a pharmaceutically acceptable salt thereof.

10. The method of claim 9 wherein the tumor necrosis factor antagonist is a tumor necrosis factor soluble receptor (TNFsr) or a pharmaceutically acceptable salt.

11. The method of claim 9 wherein the combination is suspended in an acceptable carrier.

12. The method of claim 9 wherein the tumor necrosis factor soluble receptor is a recombinant tumor necrosis factor soluble receptor (rTNFsr).

13. The method of claim 12 wherein the rTNFsr is in a dimeric form.

14. The method of claim 12 wherein the effective amount of the combination administered is from 100 ng/kg body weight to 100 mg/kg body weight of the patient per day bolus, then maintaining levels of IL-1ra with continuous infusion and rTNFsr by daily intravenous injection as long as clinically indicated.

15. The method of claim 14 wherein the combination bolus administration is intravenously as a loading dose of 10 mg/kg in a total volume of 10 ml.

16. The method of claim 14 wherein the continuous infusion of IL-1ra consists of 2.0 mg/kg/hr and the daily intravenous injection of rTNFsr is a continuous infusion of 0.5 mg/kg/hr or a single bolus infusion of 2–5 mg/kg/day.

* * * * *